United States Patent [19]
Zakoshansky et al.

[11] Patent Number: 5,908,962
[45] Date of Patent: *Jun. 1, 1999

[54] CUMENE OXIDATION PROCESS

[75] Inventors: Vladimir Mikhailovich Zakoshansky, Mt. Vernon, Ind.; Andrei Konstantinovich Griaznov; Irina I. Vasilieva, both of St. Petersburg, Russian Federation; John W. Fulmer, Mt. Vernon; William D. Kight, Poseyville, both of Ind.

[73] Assignee: General Electric Company and Illa International, Pittsfield, Mass.

[ * ] Notice: This patent is subject to a terminal disclaimer.

[21] Appl. No.: 09/020,395

[22] Filed: Feb. 9, 1998

Related U.S. Application Data

[62] Division of application No. 08/670,304, Jun. 27, 1996, Pat. No. 5,767,322.

[51] Int. Cl.$^6$ .................................................. C07C 409/10
[52] U.S. Cl. .............................................. 568/571; 568/573
[58] Field of Search ...................................... 568/571, 573

[56] References Cited

U.S. PATENT DOCUMENTS 5,767,322  6/1998  Zakoshansky ........................... 568/571

*Primary Examiner*—Gary Geist
*Assistant Examiner*—Jean F Vollano

[57] ABSTRACT

Greater efficiency in a water-alkaline emulsion cumene oxidation process using a cascade of reactors is obtained by splitting the reactor cascade into 2 stages with the first stage utilizing $NH_4NaCO_3$ as the active carbonate in the stage containing less than 18% by weight cumene hydroperoxide and using $Na_2CO_3$ as the active carbonate in the stage containing more than 18% by weight cumene hydroperoxide. By directly injecting ammonia into a recycle stream organic acids are efficiently neutralized. A counter current water wash of the second stage also increases process efficiency by scrubbing out unwanted impurities. Control of pH in the process improves efficiency and reduces impurity levels.

13 Claims, 3 Drawing Sheets

CUMENE OXIDATION PROCESS

This application is a division of Application Ser. No. 08/670,304 filed Jun. 27, 1996, now U.S. Pat. No. 5,767,322.

This invention relates to a method for commercial production of cumene hydroperoxide (CHP) obtained by a cumene oxidation method in water-alkaline emulsion (wet oxidation process) via oxygen-containing gases, for example air or air enriched with oxygen. Oxidation is conducted in a cascade of reactors (not less than two) with a variable temperature profile. An aqueous solution of $NH_4NaCO_3$ is used as an alkaline agent at a cumene oxidation level of up to 10–12% as well as an aqueous solution of $Na_2CO_3$ at a cumene oxidation level of above 10–12%.

U.S. Pat. Nos. 2,632,773, 2663,740, 3,171,865, 3,523,977 and 3,907,901 teach that phenol gives a negative effect on the selectivity and productivity of this oxidation process. To prevent this situation several alkaline agents such as NaOH or $Na_2CO_3$ are taught in U.S. Pat. No. 3,187,055 as useful. U.S. Pat. Nos. 3,523,977 and 3,907,901 teach that bicarbonates of alkaline metals—$NaHCO_3$ and $KHCO_3$ can also be used as alkaline agents to remove phenol.

In U.S.S.R. Authors Certificates 858313 (application 2843504 priority dated Nov. 27, 1979) and 567723 (Application 2134382 priority dated May 16, 1975), a dry oxidation (non water-emulsion) process using neutral ammonium salts of organic acids such as ethyleneiaminetriacetic acid, napthenic acids, a fraction of $C_{10}$–$C_{16}$ fatty acids as well as $(NH_4)_2CO_3$ to speed-up the rate of CHP accumulation and yield is taught. Judging by the examples, said ammonium salts are used to obtain high levels of cumene conversion (above 20%).

In the conventional scheme of water-emulsion cumene oxidation, aqueous $Na_2CO_3$ solution is added to each cascade reactor according to U.S. Pat. No. 3,687,055. To reduce the rate of consumption of soda, a recycle water-salt stream which contains $Na_2CO_3$ and $NaHCO_3$ is added into these reactors. This recycle is consistent with the teachings of the patent which notes that $NaHCO_3$ can be also used for neutralization of organic acids. In fact, cumene oxidation occurs in the presence of $Na_2CO_3$—$NaHCO_3$. A simplified scheme of the prior art wet oxidation process is shown on FIG. 1. The description of this process is given below for a better understanding of the improvements of the present process and the process of the prior art.

In the prior art process the oxidation is carried out in a cascade of reactors (2 and more) as shown in FIG. 1.

Oxidizer feed comprising cumene is fed through 3 to the lower part of the first reactor (A). Fresh aqueous $Na_2CO_3$ solution through 4 and aqueous solution of recycle "carbonate" contaminated with impurities containing phenol, organic acids, sodium salt of organic acids and $NaHCO_3$ through 5 are fed to the upper part of each reactor (A, B, C and D).

Fresh cumene through 1, recycle cumene from the alphamethylstyrene (AMS) hydrogenation stage of a phenol plant through 2 and recycle cumene from the CHP concentrator II through 12 are treated with alkali (NaOH) from 13 to remove phenol, and then directed through a settler VI and to secondary settler IV, where cumene is contacted with an aqueous $Na_2CO_3/NaHCO_3$ mixture and the aqueous stream containing formed phenate goes to biotreatment through secondary settler IV.

Treatment of reactor (oxidizer) feed to remove phenol is accomplished in secondary settler IV with fresh water through 6 and off-gas condensate through 7 from condenser V. Treated mixture through 3 from secondary se into the first reactor (A) in cascade and a stream comprising cumene and cumene hydroperoxide passes through reactor A and then into the other reactors (B, C and D) through 14, 15 and 16, respectively in a series flow operation. The level of cumene hydroperoxide introduced into each subsequent reactor is greater than the level in the preceding reactor.

Oxidation in the cascade reactors (A, B, C and D) is carried out at a temperature which in each successive reactor is lower than the temperature in the previous reactor. CHP concentration from one reactor to the next goes up, thus obtaining 15–40 wt % at the outlet of the last reactor. At the higher CHP concentrations yields drop precipitously.

A part of the treated aqueous sodium carbonate solution through 8 from reactors A and B is removed from the process through treater IV and sent through 9 to biotreatment and another part flows through decanter III and 10 as recycle to treater IV and then to reactors A, B, C and D.

A stream of off gas from the reactors is added through 11 into condenser V to condense cumene and water entrained with air.

Cumene selectivity in the prior art wet process is about 92.5–93% mol under optimum conditions at a cumene conversion 20–22%.

As far as chemistry and technology are concerned, the prior art process of water-emulsion cumene oxidation is characterized by the following parameters:

1. Uses $Na_2CO_3$ as an "alkaline protection".
2. Recycles water-salt streams to all reactors.
3. Washes the reactor feed to the first reactor with fresh water (water condensate) and recycles the water-organic stream from oxidation off-gas condensation unit The sodium carbonate in the recycle water-salt stream of the prior art process is typically converted to 80–100% sodium bicarbonate by neutralization of organic acids (Table 1). These measurements are made by ion exclusion chromatography. To analyze samples for formate, acetate, bicarbonate and carbonate salts content in the aqueous from the oxidizer, the following equipment is required:

A simple isocratic pump/detector instrument such as DX100 Ion Chromatograph supplied by Dionex Corporation, Sunnyvale, Calif., U.S.A..

An ion exclusion column such as Ion Pac ICE AS1 supplied by Dionex.

An anion micromembrane suppresser.

A micromembrane installation kit such as supplied by Dionex.

An autosampler accepting septum sealed vials which at no time are open to the atmosphere such as a Gilson Model 234 Autoinjector, Alltech Model 570 Autosampler or a Dionex Model AS 3500 Autosampler.

A peristaltic pump (4 to 10 ml/min range) for the suppresser with tubing and connectors such as Model 77120-10 from Cole-Parmer.

A chromatographic data system and integrator.

The following materials are needed.

Tetrabutylammonium hydroxide available from Aldrich Chemical Co.

Heptaflorobutyric acid available from Aldrich Chemical Co.

The tetrabutylammonium hydroxide is diluted to 40% by volume in water or 1 molar in methanol and stored free of atmospheric $CO_2$. A helium sparge has been found to keep the diluted tetrabutylammonium hydroxide free of air and atmospheric $CO_2$.

TABLE 1

Aqueous Phase Samples from Oxidizers

| | | Salts content, ppm | | | |
|---|---|---|---|---|---|
| Oxidizer | pH | Formate | Acetate | Bicarbonate | Carbonate |
| A | 6.48 | 1330 | 280 | 500 | 0 |
| B | 7.87 | 1470 | 250 | 627 | 3 |
| C | 8.48 | 4350 | 1460 | 4137 | 243 |
| D | 8.50 | 4660 | 1550 | 4120 | 222 |

Experiments with cumene oxidation in the presence of $NaHCO_3$ and a comparative experiment with $Na_2CO_3$ gave a surprising reduction of process selectivity by 0.5% abs. in case of using $NaHCO_3$ (FIG. 2).

In FIG. 2, curve X is based on data points from water-emulsion cumene oxidation with $Na_2CO_3$ and curve Y is based on data points from water-emulsion cumene oxidation with $NaHCO_3$. The substantially equivalent mol % selectivity shown in FIG. 2 is unexpected as $NaHCO_3$ is a salt of a strong base and a weak acid, has a pH value>7 (~8.6), and thus should not favor the reaction of acidic CHP cleavage to phenol and acetone. Phenol in the composition of oxidation products from the above reaction inhibits oxidation with reduction of both reaction rate and selectivity.

In addition, the presence of the oxidation products of phenol which is a key process inhibitor results from incomplete neutralization of organic acids, i.e., formic and benzoic acids. This incomplete neutralization is caused by the fact that the formic and benzoic acids are organic acids which are primarily found in the organic phase and $Na_2CO_3$ and $NaHCO_3$ being salts are primarily in the water phase. With the acids in the organic phase along with the oxidation products, neutralization proceeds slowly because (i) of low $Na_2CO_3$ and $NaHCO_3$ solubility in the oxidation products; and (ii) the poor neutralization reaction of organic acids with $NaHCO_3$ if it proceeds at all.

In the present invention, it has been discovered that the injection of ammonia into the process described above in an amount at least stoichiometric to the amount of byproduct organic acids, e.g. formic acid, benzoic acid, etc., neutralizes these undesirable byproducts and, surprisingly, inhibits their formation. Further, it has been found that $NH_3$ injection increases the cumene hydroperoxide yield of a conventional wet oxidation process for preparing CHP from cumene without any other modification to the process. The in situ formation of the mixed salt by $NH_3$ addition while effective in increasing yields from a single stage process is also effective in multi stage processes as well.

Preferred embodiments described hereinafter have been found which magnify the beneficial effect of the mixed salt resulting from $NH_3$ injection on process performance. However, although these preferred embodiments provide superior results, these are not meant in any way to detract from the basic discovery of the improved results from the mixed salt formed in situ by the injection of quantities of ammonia into the cumene oxidation process whether it be by injecting the ammonia at more than one point in the process, in an aqueous recycle stream or into an aqueous sodium carbonate stream to form $NH_4NaCO_3$ and/or directly into the oxidizer vessels. There are many instances where the preferred embodiments of the present inventive process can not be installed but improved performance of the existing process is still desired. Such instances may be limited financial resources, space limitations, regulatory restrictions, etc. In these instances the replacement of prior art neutralizing agents with gaseous ammonia will pay handsome dividends and embodies the present invention in its broadest sense.

A preferred embodiment of the present invention shown in FIG. 3 consists of cumene oxidation which is conducted in a cascade of reactors (more than 2) in two stages, Stage I and Stage II, as shown within the dashed lines, wherein the oxidation at the first stage (Stage I) is carried out in reactors A and B to a cumene conversion by weight of less than about 18% preferably from about 10 to about 18% more preferably from about 10 to about 15% with the use of mixed salt $NH_4NaCO_3$. This mixed salt is preferably formed in situ by injection of $NH_3$ through line 28 into line 10 which carries the aqueous sodium carbonate solution from decanter III to secondary settler IV. The $NH_4NaCO_3$ forms almost immediately. The amount of $NH_3$ is at least stoichiometric to the organic acids in the stream. At the second oxidation stage, (Stage II) the cumene conversion attains the value of over about 18%, preferably from about 18% to about 30%, more preferably from about 18% to about 25% and only fresh aqueous $Na_2CO_3$ solution is fed into reactors C and D (Stage II) through line 4. Thus, at different stages of cumene conversion, various alkaline agents are used i.e. $NH_4NaCO_3$ in reactors A and B (Stage I) and only fresh $Na_2CO_3$ in reactors C and D (Stage II), without recycle of aqueous streams. Preferably, in reactors C and D (Stage II), fresh water (water condensate, stream 26) is added as a countercurrent to the reaction oxidate.

$NaHCO_3$ formed in the reactors of the second stage is removed from the lower part of the reactors along with water stream, separated from oxidation products in the settler III and is treated in line 10 with ammonia in an equimole ratio or in mole ratio 2:1 to the sodium bicarbonate formed in these reactors.

The formed mixed salt $NH_4NaCO_3$ in the form of a water-salt solution with pH>10.5 is added through the settler IV to the first oxidation stage.

Water/organic mixture through line 7 from off-gas condensate stage (V) is treated with $NH_3$ through line 27. The amount of added ammonia is stoichiometric to the amount of the formic and benzoic acids determined by chemical analysis. To monitor the completeness of neutralization of this mixture after mixing with $NH_3$ (stream 33), the pH is maintained within the range 8–10. Such an ammonia treatment eliminates any penetration into the oxidizers of strong organic acids along with recycle streams or losses of CHP in the form of CHP salts since the ammonium CHP salts are not formed which is in contrast with the formation of the sodium salt at the treatment of CHP with NaOH.

The results obtained are demonstrated by examples 2–3. For comparison we show as example 1 a prototype which is representative of the prior art process with the use of $Na_2CO_3$ and recycle water-carbonate solutions.

The present invention improves the yields of cumene from the wet oxidation process, improves process selectivity, reduces the level of phenol in the process streams and more effectively neutralizes the undesirable formic and benzoic acids. These surprising improvements result from replacing the neutralizing agent in the treater with $NH_4NaCO_3$, neutralizing the organic acids in the condensate from the reactors overheads, changing the reactor feeds to a two stage cascade system from the single stage cascade system of the prior art and controlling pH of the recycle water-salt streams within a narrow range.

Inventive aspects of the improved wet oxidation process of the present invention are:

(1) the in situ formation of $NH_4NaCO_3$ from the $NaHCO_3$ by $NH_3$ addition which neutralizes the organic acids, such as formic and benzoic acids, inhibits their formation and increases the cumene hydroperoxide yield (2) the cascade of reactors are configured in two stages, the first with a lower cumene conversion is fed with a recycle carbonate stream and the second with a higher cumene conversion is fed with a fresh carbonate stream and no recycle feed in one embodiment.

Figure 1:
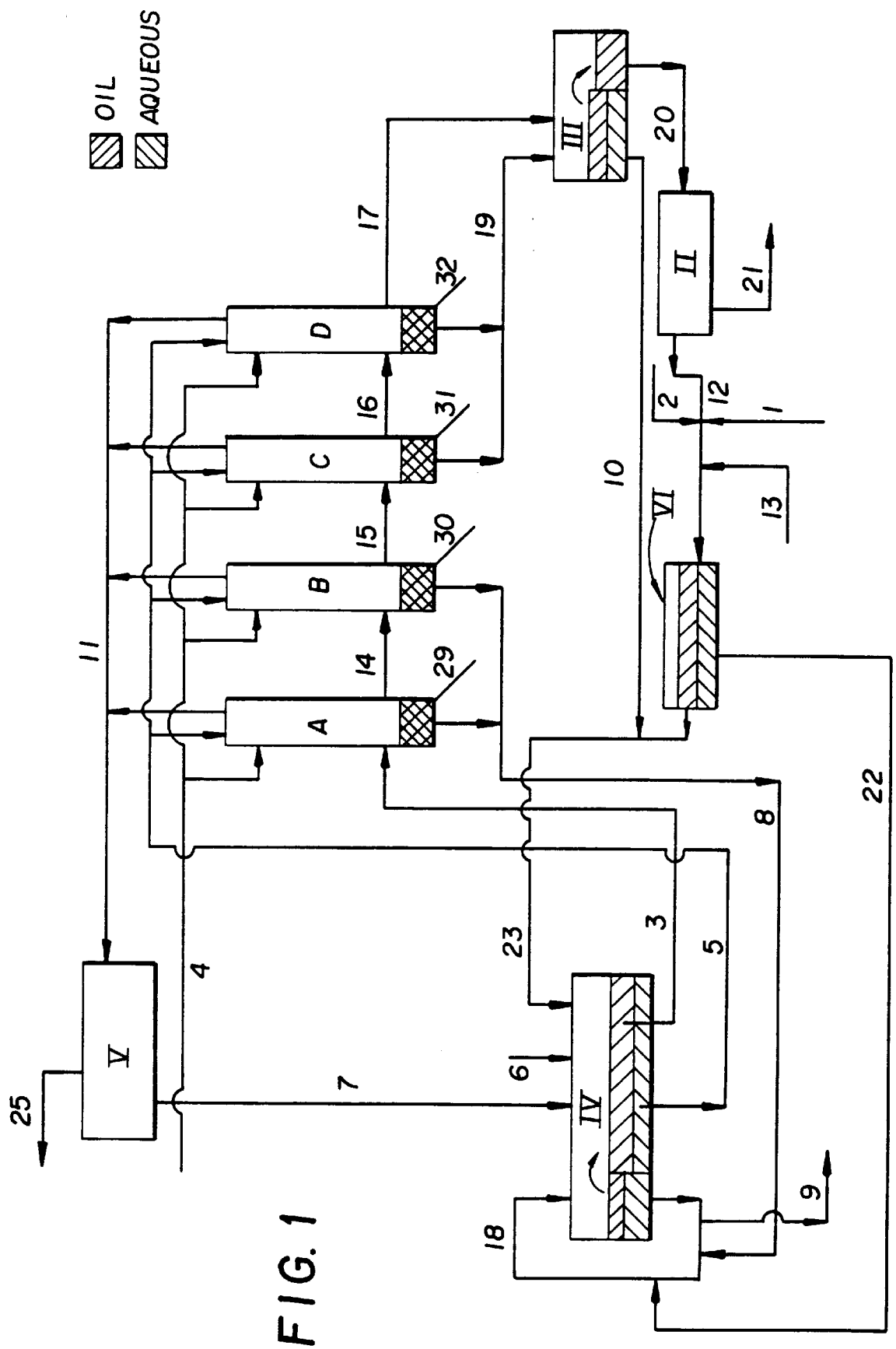
FIG. 1 is a process flow diagram of a prior art wet oxidation (water-emulsion cumene oxidation) process to make cumene hydroperoxide.

(3) in a preferred embodiment, the fresh carbonate and water stream is added to the reactors in the second stage with a higher cumene conversion as a counter-current flow to the oxidate feed stream into the reactors (4) $NaNH_4CO_3$, formed in situ from $NaHCO_3$ when ammonia is added to the recycle, more effectively neutralizes formic and benzoic acids in the recycle than does either $Na_2CO_3$ or $Na HCO_3$ alone or together as practiced in the prior art process of FIG. 1;

(5) in a preferred embodiment ammonia is injected into the process before treater IV at two different points in the process, into the gas condensate from the condenser V and into the aqueous sodium carbonate solution from the decanter III;

(6) in yet another embodiment the pH of the recycle water-salt streams is maintained preferably between 10 and 12, and more preferably between 10.5 and 11.2; and (7) measurement of levels of carbonate and bicarbonate are determined by ion exclusion chromatography analytical techniques.

Figure 3:
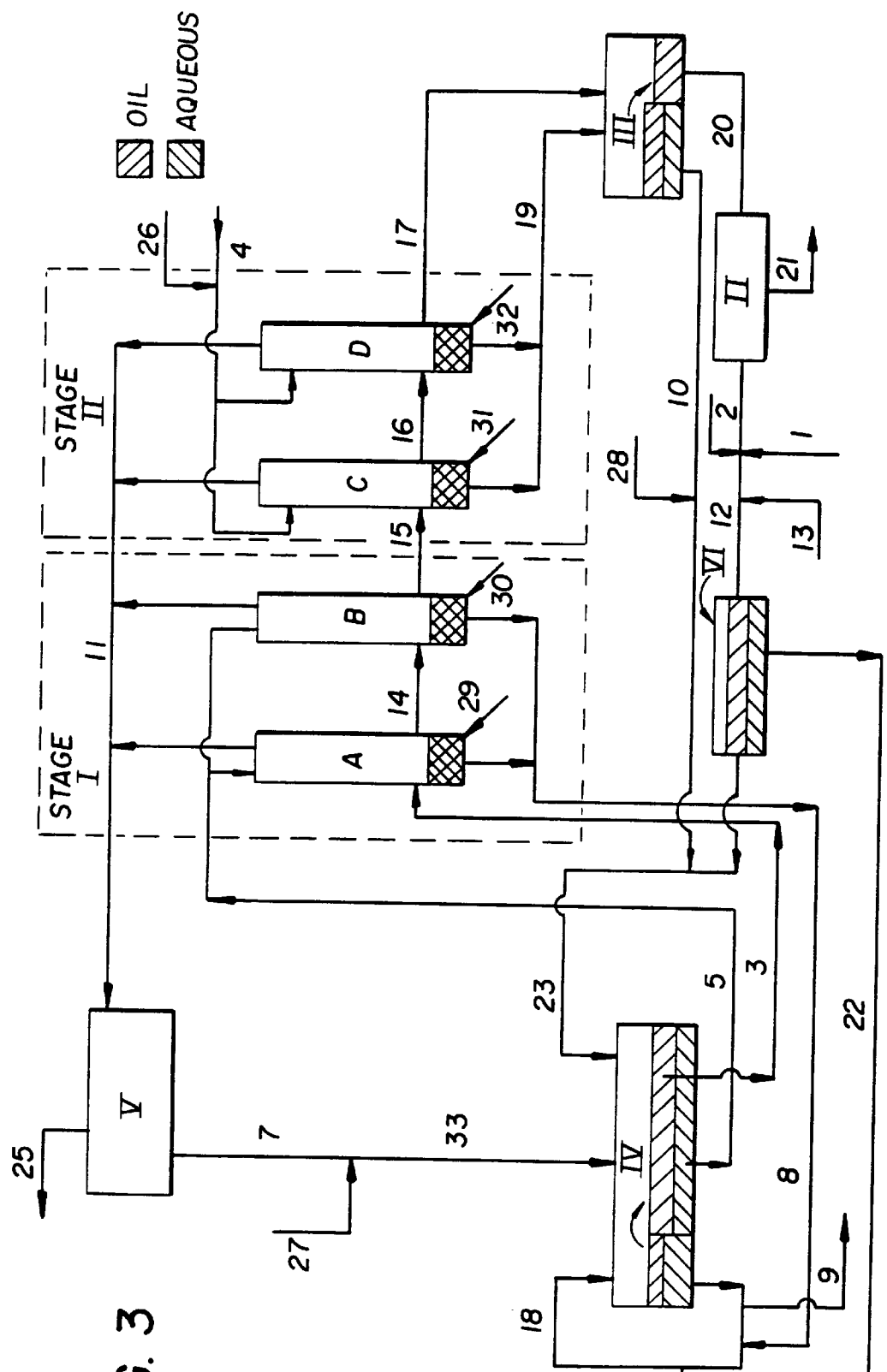
FIG. 3 is a process flow diagram of the wet oxidation (water-emulsion cumene oxidation) process of the present invention to make cumene hydroperoxide.

To be certain there is a clear understanding of FIGS. 1 and 3 of the drawing, the following is a detailed description of these figures.

FIG. 1 is a process flow diagram of the major process streams and pieces of equipment usually employed in a cumene wet-oxidation process of the prior art. Compressors, pumps and other minor equipment items are omitted.

In this prior art process, reactors A, B, C and D are the oxidizers in which cumene is oxidized to cumene hydroperoxide. In each successive reactor, the CHP content increases from about 7–8 weight percent in the first reactor to about 15–36 weight percent in the last reactor. Although four reactors are shown the number of reactors will vary from 2 to 6 or more. Since only a small percent of cumene is oxidized to CHP in each reactor the process is replete with recycle streams. Accordingly, the description of the drawing will first identify the key pieces of equipment shown as follows:

A, B, C and D reactors or oxidizers which oxidize cumene to cumene hydroperoxide II CHP concentrator which raises the level of cumene hydroperoxide in the outlet for reactor D to the minimum level required for feed to the cleavage section of the phenol plant.

III decanter which removes the aqueous phase containing carbonates and salts from the organic product stream IV secondary settler (treater) which prepares the feed for reactor A V condenser which condenses the offgases from the reactors A, B, C & D and recovers cumene and water VI settler which separates the aqueous and organic phases for recycle to the treater IV Since the wet oxidation process is well-known to the skilled artisan, the prior art process of FIG. 1 will only be described as appropriate to teach the improvements of the present invention Fresh carbonate solution ($Na_2CO_3$ in water) is added to the top of each of the reactors A, B, C and D through line 4. Oxygen, preferably as air encircled with oxygen enters the bottom of each reactor A, B, C and D through lines 29, 30, 31 and 32, respectively. From treater IV through line 3, the oxidizer feed comprising cumene and other products of oxidation enters reactor A in the lower portion. Recycle carbonate which is the aqueous layer in treater IV and which includes the impurities previously described enters the top of the reactors A, B, C and D through line 5. The wet organic layer containing CHP, cumene and impurities cascades from reactor A through line 14 to B, then from B through line 15 to C and then from C through line 16 to D. The wet organic layer then leaves D through line 17 to go to decanter III. The aqueous layer from reactors A and B recycles to recycle loop 18 of treater IV through line 8. The aqueous layer from reactors C & D recycles to decanter III through line 19. The decanted organic layer of decanter III containing about 15–36% by weight CHP goes to CHP concentrator II through line is 20. Product CHP with an assay of about 82% CHP by weight goes to the phenol plant cleavage operation through line 21. The remaining organic portion in CHP concentrator II recycles to settler VI through line 12. An alpha-methyl styrene stream containing cumene from another part of the phenol process is also added to line 12 through line 2. Fresh cumene is similarly added to line 12 through line 1 along with aqueous sodium hydroxide through line 13. From settler VI the aqueous later is recycled to the recycle loop 18 of treater IV through line 22. The organic layer is recycled directly to treater IV through line 23 along with the aqueous layer from decanter III through line 10. Spent aqueous carbonate is removed from recycle loop 18 of treater IV through line 9. The overhead spent air from each of the reactors A, B, C and D is collected in line 11 and recycled to condenser V. Non-condensables are vented through line 25. Condensate recycles to treater IV through line 7. Water is added to treater IV through line 6.

In FIG. 3, these same key pieces of equipment with the same identifying designators are shown. Lines having the same numbers as in FIG. 1 are unchanged. However, the new lines needed or old lines rerouted in order to practice the improvements of the present invention will now be described in detail.

Recycle carbonate containing $NH_4NaCO_3$ which is the aqueous layer in treater IV enters the top of only reactors A and B (Stage I) through line 5. Fresh carbonate solution in line 4 and water through line 26 enter only the top of reactors C and D (Stage II) through line 4. The countercurrent flow of water through reactors C&D scrubs the gases and improves the efficiency of water-soluble impurity removal. This prevents the organic impurities from entering reactors C and D (Stage II). Water is not added to treater IV. Ammonia ($NH_3$) is added to line 7 through line 27 and to line 10 through line 28. In line 7 the ammonia immediately and efficiently neutralizes the organic acids in the condensate from the off gases from reactors A, B, C and D. By forming water-soluble ammonium salts of these organic acids in the organic stream, these unwanted impurities are readily removed for disposal in the spent carbonate layer of treater IV through line 9 after passing through reactors A and B (Stage I). In line 10 the ammonia rapidly forms $NaNH_4CO_3$ which further enhances neutralization of organic acids in the aqueous layer of treater IV.

Figure 2:
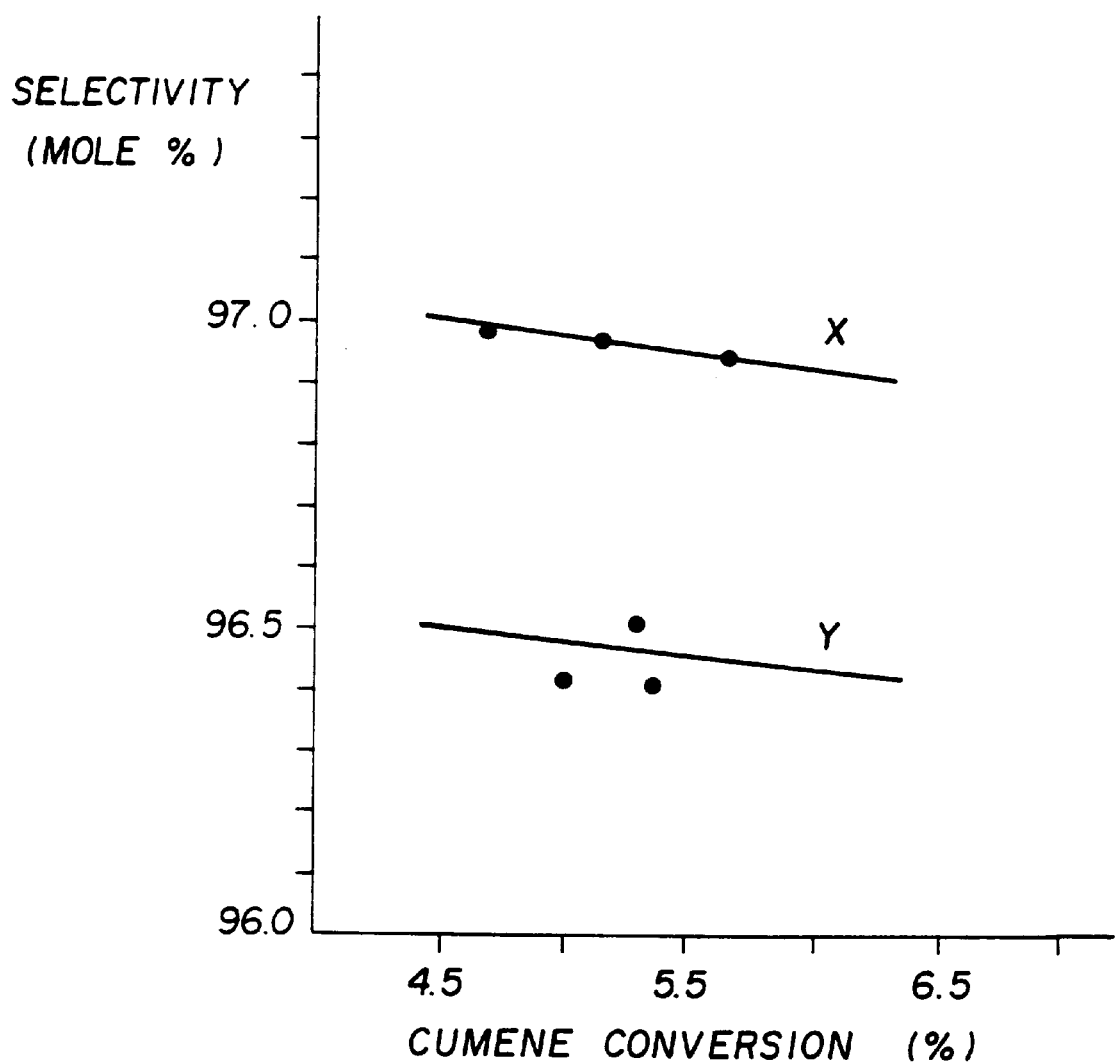
FIG. 2 is a graph comparing selectivity of a water-emulsion cumene oxidation process employing $Na_2CO_3$ and $NaHCO_3$.

Since FIG. 2 is merely a graphical representation of data points, the previous discussion of FIG. 2 is a sufficiently detailed description.

The temperature ranges in the reactors given in the examples and the number of reactors do not limit the scope of this invention. Temperature ranges and the number of reactors are not critical to the practice of the invention since the improvements are applicable to any prior art wet oxidation CHP.

Simulation under laboratory conditions was carried out with cumene of 99.9% purity.

EXAMPLES

Example 1
(for comparison)

The laboratory unit for studying the oxidation process employed a reactor made of stainless steel, of 300 mm height and of 30 mm inner diameter, and a continuous feed supply unit. In order to measure the temperature, a thermocouple temperature sensor was installed along the height of the reactor. The reactor temperature was controlled and stabilized by the temperature controller PROTERM-100. An air sparger, Shott filter, was installed in the lower part of the reactor. The pressure was controlled by the manometer installed at the reactor outlet. The air fed to the reactor was measured by a flow meter. The unit providing a continuous feed supply of the hydrocarbon phase includes feed vessels which are joined in series and a glass burette for measuring the feed consumption as well as a microdosing pump. The aqueous water/salt stream was continuously fed via a separate small dosing pump. The weight ratio of aqueous to organic phase is given in Table 2.

When studying the prior art oxidation process in the reactor cascade each reactor of the cascade was studied subsequently. For studying each subsequent reactor the oxidate produced while studying the preceding one was used as a feed.

This example provides the comparative data of the laboratory test of prior art water-emulsion cumene oxidation in a cascade of 6 reactors.

The oxidizer feed for studying the oxidation process in the first reactor was prepared by mixing pure cumene and the recycle cumene produced from the CHP concentration stage in a ratio of 1:3. The oxidizer feed which was produced was treated with 3% aqueous sodium hydroxide solution and 3% aqueous solution of sodium carbonate and sodium bicarbonate, and then washed with water and separated from the water. The oxidizer feed prepared in such a way had pH=7 and the following composition, wt %: cumene-99.06, AP-0.043, DMBA-0.17, CHP-0.72.

When studying the prior art water-emulsion oxidation process in the laboratory the process parameters corresponding to those of a commercial unit were maintained. The mixture of fresh 10% aqueous sodium carbonate solution and water recycle carbonate were mixed and used as a water-salt feed stream.

TABLE 2

| | ONE STAGE | | | | | |
|---|---|---|---|---|---|---|
| Process parameters | 1st reactor | 2nd reactor | 3rd reactor | 4th reactor | 5th reactor | 6th reactor |
| Temperature °C. | 107.2 | 102.7 | 99 | 95.5 | 93 | 92 |
| Pressure above atm. | 5 | 5 | 5 | 5 | 5 | 5 |
| Selectivity, mole % | 91.8 | 92.9 | 92.8 | 92.7 | 92.6 | 92.5 |
| Cumene conversion, mole % | 5.4 | 9.0 | 13.2 | 16.4 | 19.1 | 21.9 |
| CHP concentration wt % | 6.3 | 10.7 | 15.7 | 19.4 | 22.6 | 25.9 |
| Weight ratio of water-salt phase to organic phase. | 3.5 | 3.3 | 3.1 | 0.5 | 0.4 | 0.3 |

Material balance:

| Inputs to the process | | Outputs from the process | |
|---|---|---|---|
| fresh cumene | 215 gr | cumene | 621.58 gr |
| recycle cumene | 645 gr | DMBA | 13.40 |
| | | AP | 2.32 gr |
| | | CHP | 222.7 gr |

Example 2

The study of the oxidation process of the present invention was carried out in the same way as the prior art process described in Example 1. But in this second example the first stage of the process (the first two reactors of the cascade) used treated recycle carbonate solution. This solution contained 0.7 wt % of sodium bicarbonate and was treated with the aqueous ammonia solution (5 wt % of ammonia) in an equimolar (1:1) ratio to sodium bicarbonate (water-salt solution A). A mixture of 0.7% aqueous sodium carbonate and water-salt solution A in a ratio of 1:1 was fed to the third reactor of the reactor system ($1^{st}$ stage) as a water-salt solution. At the second stage of the process (the last three reactors of the cascade) 0.7% aqueous sodium carbonate solution and fresh water were fed to the oxidation reactors. The ratio of the water-salt solution and organic phase is shown in Table 3.

TABLE 3

| | Stage I | | | Stage II | | |
|---|---|---|---|---|---|---|
| Process parameters | 1st reactor | 2nd reactor | 3rd reactor | 4th reactor | 5th reactor | 6th reactor |
| Temperature °C. | 107.2 | 102.7 | 99 | 95.5 | 93 | 92 |
| Pressure, above atm. | 5 | 5 | 5 | 5 | 5 | 5 |
| Selectivity, mole % | 93.3 | 94.0 | 94.2 | 93.9 | 93.8 | 93.7 |
| Cumene conversion, mole % | 5.3 | 9.0 | 13.2 | 16.3 | 19.0 | 21.8 |
| CHP concentration | 6.3 | 10.7 | 15.7 | 19.4 | 22.6 | 25.9 |
| Weight ratio of water-salt phase to organic phase | 3.0 | 2.8 | 2.6 | 0.7 | 0.6 | 0.4 |

Material balance:

Inputs to the process    Outputs from the process

TABLE 3-continued

| fresh cumene | 215 gr | cumene | 625.2 |
| recycle cumene | 645 gr | DMBA | 10.4 |
| | | AP | 1.7 gr |
| | | CHP | 222.7 gr |

Example 3

The study of the oxidation process was carried out in the same way as the process described in Example 2. But in this third example the recycle aqueous carbonate solution containing 0.7 wt % bicarbonate was treated with an aqueous ammonia solution in the mole ratio 1:2. The data obtained are shown in Table 4.

TABLE 4

| | Stage I | | | Stage II | | |
|---|---|---|---|---|---|---|
| Process parameters | 1st reactor | 2nd reactor | 3rd reactor | 4th reactor | 5th reactor | 6th reactor |
| Temperature ° C. | 107.2 | 102.7 | 99 | 95.5 | 93 | 92 |
| Pressure, above atm. | 5 | 5 | 5 | 5 | 5 | 5 |
| Selectivity, mole % | 93.7 | 94.4 | 94.7 | 94.29 | 94.1 | 94 |
| Cumene conversion, mole % | 5.3 | 9.0 | 13.2 | 16.3 | 19.0 | 21.8 |
| CHP concentration wt % | 6.3 | 10.7 | 15.7 | 19.4 | 22.6 | 25.9 |
| Weight ratio of water-salt phase to organic phase. | 3.0 | 2.8 | 2.6 | 0.7 | 0.6 | 0.4 |

Material balance:

| Inputs to the process | | Outputs from the process | |
|---|---|---|---|
| fresh cumene | 215 gr | cumene | 621.1 |
| recycle cumene | 645 gr | DMBA | 9.65 |
| | | AP | 1.55 gr |
| | | CHP | 222.7 gr |

We claim:

1. An improved process for producing cumene hydroperoxide by oxidation of cumene in a water-alkaline emulsion which produces organic acids as undesired byproducts wherein the improvement comprises injecting $NH_3$ in an amount at least stoichiometric to the amount of byproduct organic acids.

2. The process of claim 1 wherein the $NH_3$ is injected into an aqueous sodium carbonate solution and forms $NH_4NaCO_3$.

3. The process of claim 1 wherein the level of organic acid salts formed is determined by ion exclusion chromatograph.

4. The process of claim 1 wherein the oxidation is in a first and second stage.

5. The process of claim 2 wherein about 10 to about 18 percent by weight of the cumene is converted in the first stage.

6. The process of claim 4 wherein fresh aqueous $Na_2CO_3$ is fed only into the second stage.

7. The process of claim 6 wherein the fresh aqueous $Na_2CO_3$ is fed countercurrent to the oxidate stream.

8. The process of claim 7 wherein water is added along with the fresh aqueous $Na_2CO_3$.

9. The process of claim 4 wherein the $NH_3$ is injected into a recycle aqueous stream from the second stage.

10. The process of claim 4 wherein the $NH_3$ is injected into recycle aqueous streams from both the first and second stages.

11. The process of claim 9 wherein the pH of the recycle aqueous stream is controlled between about 10 and about 12.

12. The method of claim 4 wherein an aqueous $NH_4NaCO_3$ is obtained by adding ammonium hydroxide to neutralized acid by-products of the second stage.

13. The method of claim 1 wherein the oxidation is conducted in oxidizer vessels and the $NH_3$ is injected directly into the oxidizer vessels.

* * * * *